United States Patent [19]
Isenring et al.

[11] Patent Number: 5,965,613
[45] Date of Patent: *Oct. 12, 1999

[54] DERIVATIVES OF ACRYLIC ACID

[75] Inventors: Hans P. Isenring, Sissach, Switzerland; Stephan Trah, Freiburg, Germany; Bettina Drechsel, Basel, Switzerland

[73] Assignee: Novartis Finance Corporation, New York, N.Y.

[*] Notice: This patent is subject to a terminal disclaimer.

[21] Appl. No.: 08/935,208

[22] Filed: Sep. 22, 1997

Related U.S. Application Data

[63] Continuation-in-part of application No. 08/727,329, Oct. 8, 1996, abandoned, which is a continuation of application No. 08/518,476, Aug. 21, 1995, abandoned, which is a continuation of application No. 07/954,842, Sep. 30, 1992, abandoned, which is a continuation of application No. 07/853,227, Mar. 13, 1992, abandoned, which is a continuation of application No. 07/555,427, Aug. 20, 1990, abandoned, which is a continuation of application No. PCT/CH89/00216, Dec. 12, 1989.

[51] Int. Cl.⁶ .......... A01N 37/44; C07C 255/09; C07C 229/32
[52] U.S. Cl. ............ 514/538; 558/391; 560/35
[58] Field of Search .......... 504/312; 558/391; 560/35; 514/530

[56] References Cited

U.S. PATENT DOCUMENTS 5,756,426  5/1998  Ziegler et al. .......... 504/312

Primary Examiner—Johann Richter
Assistant Examiner—Ebenzer Sackey
Attorney, Agent, or Firm—Michael P. Morris

[57] ABSTRACT

The present invention relates to aromatic compounds, namely substituted methyl 2-phenyl-3-methoxy-acrylates of the general formula

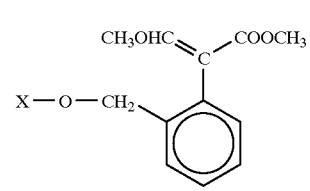

I where X represents an aldimino or ketimino group, in particular a group

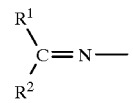

where $R^1$ and $R^2$ independently of one another denote hydrogen, $C_{1-12}$-alkyl, $C_{1-4}$-haloalkyl, and $C_{1-4}$-alkoxy-$C_1$–$C_4$-alcyl.

15 Claims, No Drawings

DERIVATIVES OF ACRYLIC ACID

CROSS REFERENCE TO RELATED APPLICATION

This a continuation-in-part of application Ser. No. 08/727,329, filed Oct. 8, 1996, now abandoned, which is a continuation of application Ser. No. 08/518,476, filed Aug. 21, 1995 now abandoned, which is a continuation of application Ser. No. 07/954,842, filed Sep. 30, 1992 now abandoned, which is a continuation of application Ser. No. 07/853,227, filed Mar. 13, 1992, now abandoned, which is a continuation of application Ser. No. 07/555,427, filed Aug. 20, 1990, now abandoned, and PCT/CH89/00216, filed Dec. 12, 1989.

DETAILED DESCRIPTION

The present invention relates to aromatic compounds, namely substituted methyl 2-phenyl-3-methoxy-crylates of the general formula

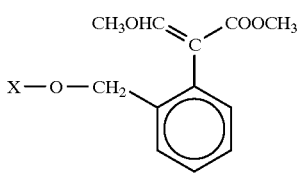

where X represents an aldimino or ketimino group, in particular a group

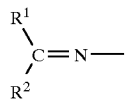

where $R^1$ and $R^2$ independently of one another denote hydrogen, $C_{1-12}$-alkyl, $C_{1-4}$-haloalkyl, $C_{1-4}$-alkoxy-$C_{1-4}$-alkyl, $C_{1-4}$-alkylthio-$C_{1-4}$-alkyl, aryl-$C_{1-4}$-alkyl, aryloxy-$C_{1-4}$-alkyl, arylthio-$C_{1-4}$-alkyl, heteroaryl-$C_{1-4}$-alkyl, $C_{2-12}$-alkenyl, aryl-$C_{2-4}$-alkenyl, heteroaryl-$C_{2-4}$-alkenyl, $C_{2-12}$-alkynyl, $C_{3-6}$-cycloalkyl, aryl, heteroaryl, cyano or one of the groups (a) to (d)

COOR³ (a)

CONR⁴R⁵ (b)

COR⁶ (c)

CR⁷=NOR⁸ (d)

or $R^1$ and $R^2$ together with the carbon atom to which they are attached denote a 4–7-membered ring which optionally contains an oxygen or sulphur atom and which can contain one or two fused aromatic rings, for example optionally substituted benzene rings, and $R^3$, $R^4$, $R^5$, $R^6$, $R^7$ and $R^8$ in each case denote hydrogen, $C_{1-4}$-alkyl, aryl or heteroaryl.

The compounds according to the invention have fungicidal properties and are suitable as fungicidal active substances, in particular for use in agriculture and horticulture. The compounds also have insecticidal and acaricidal activity.

The invention furthermore relates to a process for the manufacture of the compounds according to the invention, to compositions which contain such compounds as active substances, and to the use of such compounds and compositions for controlling fungi, insects, and acarids.

In the above formula I, all the "alkyl", "alkenyl" and "alkynyl" groups, as such or as a component of larger groups, for example heteroarylalkyl, can be straight-chain or branched, depending on the number of carbon atoms they contain. In addition, the alkenyl and alkynyl groups can in each case have more than one double or triple bond. A halogen atom which may be present is fluorine, chlorine, bromine or iodine, fluorine, chlorine and bromine being preferred. A group, such as, for example, alkyl, as such or as a component of a larger group which in each case has more than one halogen substituent, can have identical or different halogen atoms. Aryl is taken to mean, in particular, phenyl, naphthyl, phenanthryl or fluorenyl, heteroaryl is taken to mean a heterocyclic group having aromatic character, such as pyrrolyl, pyridyl, furyl, thienyl, isoxazolyl, thiazolyl, imidazolyl, pyrimidinyl or triazolyl, or such a group with a benzene nucleus fused to it, for example quinolinyl, benzofuryl, benzothienyl or dibenzofuryl. This also applies to aryl or heteroaryl as part of a larger group, for example aralkyl or heteroarylalkyl. The aryl and heteroaryl groups can in each case have one or more substituents, this substituent or these substituents being suitably selected from amongst halogen, $C_{1-4}$-alkyl, $C_{1-4}$-haloalkyl, $C_{1-4}$-alkoxy-$C_{1-4}$-alkyl, aryl-$C_{1-4}$-alkyl, heteroaryl-$C_{1-4}$-alkyl, aryloxy-$C_{1-4}$-alkyl, heteroaryloxy-$C_{1-4}$-alkyl, $C_{2-4}$-alkenyl, aryl-$C_{2-4}$-alkenyl, heteroaryl-$C_{2-4}$-alkenyl, $C_{2-4}$-alkynyl, $C_{3-6}$-cycloalkyl, aryl, heteroaryl, $C_{1-4}$-alkoxy, $C_{1-4}$-haloalkoxy, aryl-$C_{1-4}$-alkoxy, heteroaryl-$C_{1-4}$-alkoxy, $C_{2-4}$-alkenyloxy, $C_{2-4}$-alkynyloxy, aryloxy, heteroaryloxy, $C_{1-4}$-alkylthio, cyano, nitro, a group $NR^9R^{10}$, a group $COR^{11}$ and a group $COOR^{12}$ (where $R^9$, $R^{10}$, $R^{11}$ and $R^{12}$ in each case denote $C_{1-4}$-alkyl, aryl or heteroaryl).

If the compounds of the formula I have asymmetric carbon atoms, the compounds occur in optically active form. By virtue of the aliphatic and the imino double bond alone, the compounds occur in any case in the [E] or [Z] form. It is also possible that atropisomerism occurs. Formula I is intended to embrace all these possible isomeric forms as well as their mixtures, for example racemic mixtures and any [E/Z] mixtures.

A particular group of compounds of the formula I consists of those compounds of the formula I in which X denotes a group $R^1R^2C=N—$, where $R^1$ and $R^2$ independently of one another denote hydrogen, $C_{1-12}$-alkyl, $C_{1-4}$-haloalkyl, aryl-$C_{1-4}$-alkyl, heteroaryl-$C_{1-4}$-alkyl, $C_{2-12}$-alkenyl, aryl-$C_{2-4}$-alkenyl, heteroaryl-$C_{2-4}$-alkenyl, $C_{2-12}$-alkynyl, $C_{3-6}$-cycloalkyl, aryl, heteroaryl, cyano or one of the abovementioned groups (a) to (d), or $R^1$ and $R^2$ together with the carbon atom to which they are attached denote a ring as defined in greater detail above.

In the group $R^1R^2C=N—$, $R^1$ and $R^2$ being independent of one another, $R^1$ preferably denotes optionally substituted phenyl, any substituents which may be present preferably being up to three identical or different halogen atoms (in particular fluorine, chlorine and/or bromine), $C_{1-4}$-alkyl groups (in particular methyl), $C_{1-4}$-haloalkyl groups (in particular trifluoromethyl) and/or $C_{1-4}$-halolkoxy groups (in particular trifluoromethoxy), and $R^2$ preferably denotes hydrogen, $C_{1-12}$-alkyl (in particular ethyl or ethyl), C1–4-haloalkyl (in particular trifluoromethyl) or $C_{3-6}$-cycloalkyl (in particular cyclopropyl).

$R^1$ likewise preferably denotes heteroaryl, in particular furyl which is optionally substituted with up to two methyl groups, thienyl which is optionally substituted with chlorine or methyl, or benzofuryl, and $R^2$ likewise preferably denotes methyl.

In general, the [E] forms of the compounds of the formula I are preferred to the [Z] forms.

Particularly preferred individual compounds of the formula I are:

methyl 3-methoxy-2-[α-{[(α-methyl-benzyl)imino]oxy}-o-tolyl]-acrylate, methyl 3-methoxy-2-[α-{[(α-methyl-3,5-di-trifluoromethyl-benzyl)imino]oxy}-o-tolyl]-acrylate, methyl 3-methoxy-2-[α-{[(α-methyl-2-fluoro-5-methyl-benzyl)imino]oxy}-o-tolyl]-acrylate, methyl 1-[α-{[(1-[2-benzofuryl]-ethyl)imino]oxy}-o-tolyl]-3-methoxy-acrylate, methyl 3-methoxy-2-[α-{[(3-nitrobenzyl)imino]oxy}-o-tolyl]-acrylate, methyl 3-methoxy-2-[α-{[(α-trifluoromethyl-benzyl)imino]oxy}-o-tolyl]-acrylate, methyl 3-methoxy-2-[α-{[(α-methyl-4-fluorobenzyl)imino]oxy}-o-tolyl]-acrylate, methyl 3-methoxy-2-[α-{[(1-[2-thienyl]-ethyl)-imino]oxy}-o-tolyl]-acrylate, methyl 3-methoxy-2-[α-{[(α-methyl-4-chlorobenzyl)imino]oxy}-o-tolyl]-acrylate, methyl 2-[α-{[(α-cyclopropyl-benzyl)imino]oxy}-o-tolyl]-3-methoxy-acrylate, methyl 2-[α-{[(1-[5-chloro-2-thienyl]-ethyl)-imino]oxy}-o-tolyl]-3-methoxy-acrylate, methyl 3-methoxy-2-[α-{[(α-methyl-3-trifluoromethyl-benzyl)imino]oxy}-o-tolyl]-acrylate, methyl 3-methoxy-2-[α-{[(α-methyl-3-bromobenzyl)-imino]oxy}-o-tolyl]-acrylate, methyl 2-[α-{[(1-[3,5-dimethyl-2-furyl]-ethyl)-imino]oxy}-o-tolyl]-3-methoxy-acrylate, methyl 2-[α-{[(1-[2,5-dimethyl-3-thienyl]-ethyl)-imino]oxy}-o-tolyl]-3-methoxy-acrylate, methyl 3-methoxy-2-[α-{[(α-methyl-3-chlorobenzyl)-imino]oxy}-o-tolyl]-acrylate, methyl 3-methoxy-2-[α-{[(α-methyl-3-methylbenzyl)-imino]oxy}-o-tolyl]-acrylate, methyl 3-methoxy-2-[α-{[(α-methyl-4-methylbenzyl)-imino]oxy}-o-tolyl]-acrylate, methyl 2-[α-{[(3-fluorobenzyl)imino]oxy}-o-tolyl]-3-methoxy-acrylate, methyl 3-methoxy-2-[α-{[(α-methyl-4-trifluoromethyl-benzyl)imino]oxy}-o-tolyl]-acrylate, methyl 3-methoxy-2-[α-{[(α-methyl-3-fluoro-5-trifluoromethyl-benzyl)imino]oxy}-o-tolyl]-acrylate, methyl 3-methoxy-2-[α-{[(α-methyl-3-fluorobenzyl)-imino]oxy}-o-tolyl]-acrylate, methyl 3-methoxy-2-[α-{[(α-methyl-3-trifluoromethoxy-benzyl)imino]oxy}-o-tolyl]-acrylate and methyl 2-[α-{[(α-ethyl-3-trifluoromethyl-benzyl)-imino]oxy}-o-tolyl]-3-methoxy-acrylate.

Other preferred individual compounds of the formula I are:

methyl 2-[α-{[(1-[2-furyl]-ethyl)imino]oxy}-o-tolyl]-3-methoxy-acrylate, methyl 3-methoxy-2-[α-{[(1-[2-naphthyl]-ethyl)-imino]oxy}-o-tolyl]-acrylate, methyl 2-[α-{[(4-chlorobenzyl)imino]oxy}-o-tolyl]-3-methoxy-acrylate, methyl 2-[α-{[(2,4-dichlorobenzyl)imino]oxy}-o-tolyl]-3-methoxy-acrylate, methyl 3-methoxy-2-[α-{[(α-methyl-4-nitrobenzyl)-imino]oxy}-o-tolyl]-acrylate, methyl 2-[α-{(benzylimino)oxy}-o-tolyl]-3-methoxy-acrylate, methyl 3-methoxy-2-[α-{[(2-pyridylmethyl)imino]oxy}-o-tolyl]-acrylate, methyl 2-[α-{[(α-ethyl-benzyl)imino]oxy}-o-tolyl]-3-methoxy-acrylate, methyl 2-[α-{[(α-ethyl-4-chlorobenzyl)imino]oxy}-o-tolyl]-3-methoxy-acrylate, methyl 3-methoxy-2-[α-{[(α-[n-propyl]-benzyl)-imino]oxy}-o-tolyl]-acrylate, methyl 2-[α-{[(1[-benzoyl]-ethyl)imino]oxy}-o-tolyl]-3-methoxy-acrylate, methyl 3-methoxy-2-[α-{[(α-methyl-γ-phenyl-allyl)-imino]oxy}-o-tolyl]-acrylate, methyl 3-methoxy-2-[α-{[(α-methyl-4-phenoxy-benzyl)imino]oxy}-o-tolyl]-acrylate, methyl 2-[α-{[(α-cyclopropyl-4-chlorobenzyl)-imino]oxy}-o-tolyl]-3-methoxy-acrylate, methyl 3-methoxy-2-[α-{[(1-[2-pyridyl]-ethyl)-imino]oxy}-o-tolyl]-acrylate, methyl 3-methoxy-2-[α-{[(1-[3-pyridyl]-ethyl)-imino]oxy}-o-tolyl]-acrylate, methyl 3-methoxy-2-[α-{[(1-[5-methyl-2-furyl]-ethyl)imino]oxy}-o-tolyl]-acrylate, methyl 2-[α-{[(dicyclopropylmethyl)imino]oxy}-o-tolyl]-3-methoxy-acrylate, methyl 3-methoxy-2-[α-{[(2-naphthylmethyl)imino]oxy}-o-tolyl]-3-methoxy-acrylate, methyl 3-methoxy-2-[α-{[(α-methyl-3-nitrobenzyl)-imino]oxy}-o-tolyl]-acrylate, methyl 2-[α-{[(1-[2,4-dimethyl-5-thiazolyl]-ethyl)imino]oxy}-o-tolyl]-3-methoxy-acrylate, methyl 3-methoxy-2-[α-{[(α-methyl-4-methoxy-benzyl)imino]oxy}-o-tolyl]-acrylate, methyl 3-methoxy-2-[α-{[(α-methyl-3,4-dichlorobenzyl)imino]oxy}-o-tolyl]-acrylate, methyl 3-methoxy-2-[α-{[(α-methyl-2-fluorobenzyl)-imino]oxy}-o-tolyl]-acrylate, methyl 3-methoxy-2-[α-{[(α-methyl-2,4-dimethyl-benzyl)imino]oxy}-o-tolyl]-acrylate, methyl 3-methoxy-2-[α-{[(α-methyl-4-ethylbenzyl)-imino]oxy}-o-tolyl]-acrylate, methyl 3-methoxy-2-[α-{[(α-methyl-3-ethylbenzyl)-imino]oxy}-o-tolyl]-acrylate, methyl 3-methoxy-2-[α-{[(α-methyl-3,4-dimethyl-benzyl)imino]oxy}-o-tolyl]-acrylate, methyl 2-[α-{[(1-[5-bromo-2-thienyl]-ethyl)imino]oxy}-o-tolyl]-3-methoxy-acrylate, methyl 3-methoxy-2-[α-{[(1-[2-naphthyl]-propyl)-imino]oxy}-o-tolyl]-acrylate and methyl 2-[α-{[(α-cyclopropyl-2-naphthylmethyl)-imino]oxy}-o-tolyl]-3-methoxy-acrylate.

Other representatives of compounds of the formula I are:

methyl 3-methoxy-2-[α-{[(α-methyl-2,3-difluoro-benzyl)imino]oxy}-o-tolyl]-acrylate, methyl 3-methoxy-2-[α-{[(α-methyl-2,4-difluoro-benzyl)imino]oxy}-o-tolyl]-acrylate, methyl 3-methoxy-2-[α-{[(α-methyl-2,5-difluoro-benzyl)imino]oxy}-o-tolyl]-acrylate, methyl 3-methoxy-2-[α-{[(α-methyl-3,4-difluoro-benzyl)imino]oxy}-o-tolyl]-acrylate, methyl 3-methoxy-2-[α-{[(α-trifluoromethyl-carbonyl-2,
3-dichlorobenzyl)imino]oxy}-o-tolyl]-acrylate,
methyl 3-methoxy-2-[α-{[(α-trifluoromethyl-2,3-
dichlorobenzoylmethyl)imino]oxy}-o-tolyl]-acrylate,
methyl 3-methoxy-2-[α-{[(1-methyl-2-phenoxy-propyl)
imino]oxy}-o-tolyl]-acrylate,
methyl 3-methoxy-2-[α-{[(1-methyl-2-[2-
chlorophenoxy]-propyl)imino]oxy}-o-tolyl]-acrylate,
methyl 3-methoxy-2-[α-{[(1-methyl-2-phenylthiopropyl)
imino]oxy}-o-tolyl]-acrylate,
methyl 3-methoxy-2-[α-{[(α-trifluoromethyl-carbonyl-2-
naphthylmethyl)imino]oxy}-o-tolyl]-acrylate,
methyl 2-[α-{[(α-cyclopropylcarbonyl-2-
naphthylmethyl)imino]oxy}-o-tolyl]-3-methoxy-
acrylate,
methyl 2-[α-{[(α-isopropyl-2-naphthylmethyl)-imino]
oxy}-o-tolyl]-3-methoxy-acrylate,
methyl 2-[α-{[(α-dimethylaminomethyl-2-naphthyl-
methyl)imino]oxy}-o-tolyl]-3-methoxy-acrylate and
methyl 3-methoxy-2-[α-{[(2,4,4-trimethyl-1-cyclohexen-
6-yl)imino]oxy}-o-tolyl]-acrylate.

The process according to the invention for the manufacture of the compounds according to the invention is characterized in that an oxime X—OH, in particular an oxime of the general formula

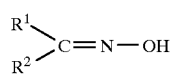

II where R¹ and R² have the abovementioned meanings is reacted with a benzyl alcohol derivative of the general formula

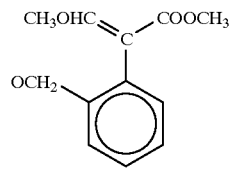

III where U denotes a leaving group.

This reaction is a nucleophilic substitution which can be carried out under the reaction conditions customary for such substitutions. The leaving group U in the benzyl alcohol derivative of the formula III is preferably taken to mean chlorine, bromine, iodine, mesyloxy or tosyloxy. The reaction is suitably carried out in an inert organic diluent, such as a cyclic ether, for example tetrahydrofuran or dioxan, acetone, dimethyl formamide or dimethyl sulphoxide, in the presence of a base, such as sodium hydride, sodium carbonate or potassium carbonate, of a tertiary amine, for example a trialkyl amine, in particular diazabicyclononane or diazabicycloundecane, or silver oxide, at temperatures between −20° C. and 80° C., preferably in the temperature range from 0° C. to 20° C.

Alternatively, the reaction can be carried out under phase transfer catalysis at room temperature in an organic solvent, such as, for example, methylene chloride, in the presence of an aqueous basic solution, for example sodium hydroxide solution, and of a phase transfer catalyst, such as, for example, tetrabutylammonium bisulphate.

The resulting compounds of the formula I can be isolated and purified by methods known per se. Any mixtures of isomers which are obtained, for example mixtures of E/Z isomers, can be separated to give the pure isomers likewise by methods known per se, for example by chromatography or fractional crystallisation.

The oximes X—OH which are used as starting materials in the process according to the invention, for example those of the formula II, are either known or they can be produced by methods known per se, for example by reacting the corresponding carbonyl compound $R^1R^2C=O$ with hydroxylamine hydrochloride in the presence of a base, for example sodium hydroxide, potassium hydroxide or pyridine. For other methods, see Houben-Weyl, "Methoden der Organischen Chemie" ["Methods of Organic Chemistry"], volume X/4, pages 3–308 (1968) ("Herstellung und Umwandlung von Oximen" ["Preparation and Conversion of Oximes"]).

Likewise, the starting materials of the formula III can be produced in a manner known per se, for example as described in European Patent Publication No. 203,606 (BASF) and in the references quoted therein.

The compounds according to the invention have fungicidal activity and can accordingly be used for controlling fungi in agriculture, horticulture and wood processing. They are particularly suitable for inhibiting the growth of, or destroying, phytopathogenic fungi on parts of plants, for example leaves, stems, roots, tubers, fruits or flowers, and on seeds, and for inhibiting the growth of, or destroying, pathogenic fungi which occur in the soil. It is furthermore possible to control wood-destroying and wood-discolouring fungi with the compounds according to the invention. For example, the compounds according to the invention are active in the control of fungi of the classes of the Deuteromycetes, Ascomycetes, Basidiomycetes and Phycomycetes.

The compounds according to the invention are particularly suitable for controlling the following pathogens:

Powdery mildews (for example *Erysiphe graminis, Erysiphe cichoracearum, Podosphaera leucotricha, Uncinula necator,* Sphaerotheca spp.)

Rusts (for example *Puccinia tritici, Puccinia recondita, Puccinia hordei, Puccinia coronata, Puccinia striiformis, Puccinia arachidis, Hemileia vastatrix, Uromyces fabae*)

Scabs (for example *Venturia inaequalis*)

Cercospora spp. (for example *Cercospora arachidicola, Cercospora beticola*)

Mycosphaerella spp. (for example *Mycosphaerella fijiensis*)

Alternaria spp. (for example *Alternaria brassicae, Alternaria mali*)

Septoria spp. (for example *Septoria nodorum*)

Helminthosporium spp. (for example *Helminthosporium teres, Helminthosporium oryzae*)

Plasmopara spp. (for example *Plasmopara viticola*)

Pseudoperonospora spp. (for example *Pseudoperonospora cubensis*)

Phytophtora spp. (for example *Phytophtora infestans*)

Pseudocercosporella spp. (for example *Pseudocercosporella herpotrichoides*)

Pyricularia spp. (for example *Pyricularia oryzae*)

Furthermore, the compounds are active against, for example, fungi of the genera Tilletia, Ustilago, Rhizoctonia, Verticillium, Fusarium, Pythium, Gaeumannomyces, Sclerotinia, Monilia, Botrytis, Peronospora, Bremia, Gloeosporium, Cercosporidium, Penicillium, Ceratocystis, Rhynchosporium, Pyrenophora, Diaporthe, Ramularia and Leptosphaeria. Certain representatives of the compounds according to the invention have an additional action against wood-destroying fungi, such as, for example, those of the genera Coniophora, Gloeophyllum, Poria, Merulius, Trametes, Aureobasidium, Sclerophoma and Trichoderma.

The compounds according to the invention are distinguished by a prophylactic and curative action.

Under greenhouse conditions, the compounds according to the invention are active against phytopathogenic fungi at concentrations of as little as 0.5 mg to 500 mg of active substance per litre of spray liquor. In the field, it is advantageous to apply dosages of 20 g to 1 kg of active substance of the formula I per hectare per treatment. To control seed-borne fungi or fungi which occur in the soil by seed-dressing, it is advantageous to use dosages of 0.01 g to 1.0 g of active substance of the formula I per kg of seed.

The compounds according to the invention can be formulated to give a range of compositions, for example solutions, suspensions, emulsions, emulsifiable concentrates and preparations in the form of powders. The fungicidal compositions according to the invention are characterized in that they contain an effective amount of at least one compound of the general formula I, as defined above, in addition to formulation adjuvants. It is expedient for the compositons to contain at least one of the following formulation adjuvants:

Solid carriers; solvents or dispersion media; tensides (wetting agents and emulsifiers); dispersing agents (without tenside action); and stabilizers.

Solid carriers which are suitable are, mainly, natural mineral substances, such as kaolin, clays, kieselguhr, talc, bentonite, chalk, for example whiting, magnesium carbonate, limestone, quartz, dolomite, attapulgite, montmorillonite and diatomaceous earth; synthetic mineral substances, such as highly-dispersed silica, alumina and silicates; organic substances, such as cellulose, starch, urea and synthetic resins; and fertilizers, such as phosphates and nitrates, it being possible for such carriers to be present, for example, as granules or powders.

Suitable solvents or dispersion media are, mainly, aromatic substances, such as toluene, xylenes, benzene and alkylnaphthalines; chlorinated aromatic substances and chlorinated aliphatic hydrocarbons, such as chlorobenzenes, chloroethylenes and methylene chloride; aliphatic hydrocarbons, such as cyclohexane, and paraffins, for example mineral oil fractions; alcohols, such as butanol and glycol, as well as their ethers and esters; ketones, such as acetone, methyl ethyl ketone, methyl isobutyl ketone and cyclohexanone; and strongly polar solvents or dispersion media, such as dimethylformamide, N-methylpyrrolidone and dimethyl sulphoxide, these solvents or dispersion media preferably having flashpoints of at least 30° C. and boiling points of at least 50° C., and water. Suitable among the solvents or dispersion media are also so-called liquefied gaseous extenders or carriers, which are those products which are gaseous at room temperature and under atmospheric pressure. Examples of such products are, in particular, aerosol propellants, such as halohydrocarbons, for example dichlorodifluoromethane. If water is used as the solvent, it is also possible to use, for example, organic solvents as auxiliary solvents.

The tensides (wetting agents and emulsifiers) can be nonionic compounds, such as condensation products of fatty acids, fatty alcohols or aliphatically substituted phenols with ethylene oxide; fatty acid esters and fatty acid ethers of sugars or polyhydric alcohols; the products which are obtained from sugars or polyhydric alcohols by condensation with ethylene oxide; block polymers of ethylene oxide and propylene oxide; or alkyldimethylamine oxides.

The tensides can also be anionic compounds, such as soaps; fatty sulphate esters, for example dodecyl sodium sulphate, octadecyl sodium sulphate and cetyl sodium sulphate; alkylsulphonates, arylsulphonates and aliphatic-aromatic sulphonates, such as alkylbenzenesulphonates, for example calcium dodecylbenzenesulphonate, and butyl-naphthalenesulphonates; and more complex fatty sulphonates, for example the amide condensation product of oleic acid and N-methyltaurine, and the sodium sulphonate of dioctyl succinate.

Finally, the tensides can be cationic compounds, such as alkyldimethylbenzylammonium chlorides, dialkyldimethy-lammonium chlorides, alkyltrimethylammonium chlorides and ethoxylated quaternary ammonium chlorides.

Suitable dispersing agents (without surfactant action) are mainly lignin, sodium salts and ammonium salts of lignin sulphonic acid, sodium salts of maleic anhydride/diisobutylene copolymers, sodium salts and ammonium salts of sulphonated polycondensation products of naphthalene and formaldehyde, and sulphite waste liquors.

Examples of dispersing agents which are particularly suitable as thickeners and anti-settling agents are methylcellulose, carboxymethylcellulose, hydroxyethylcellulose, polyvinyl alcohol, alginates, caseinates and blood albumin.

Examples of suitable stabilizers are acid-binding agents, for example epichlorohydrin, phenyl glycidyl ether and soya epoxides; antioxidants, for example gallic esters and butyl hydroxytoluene; UV absorbers, for example substituted benzophenones, diphenylacrylonitrile acid esters and cinnamic esters; and deactivators, for example salts of ethylenediamine tetraacetic acid, and polyglycols.

In addition to the active substances of the formula I, the fungicidal compositions according to the invention can also contain other active substances, for example further fungicidal agents, insecticidal and acaricidal agents, bactericides, plant growth regulators and fertilizers. Such combination compositions are suitable for broadening the spectrum of activity or for specifically influencing plant growth.

In general, the fungicidal compositions according to the invention contain, depending on their type, between 0.0001 and 85 percent by weight of compound according to the invention, or compounds according to the invention, as active substance(s). They can be in a form which is suitable for storage and transport. The concentration of active substance in such forms, for example emulsifiable concentrates, is usually in the higher range of the above concentration interval. These forms can then be diluted with the same or different formulation adjuvants down to concentrations of active substance which are suitable for use in practice, and such concentrations are usually in the lower range of the above concentration interval. In general, emulsifiable concentrates contain 5 to 85 percent, by weight, preferably 25 to 75 percent by weight, of the compound(s) according to the invention. Suitable use forms are, inter alia, ready-to-use solutions, emulsions and suspensions, which are suitable, for example, as spray liquors. Concentrations of between 0.0001 and 20 percent by weight, for example, can be present in such spray liquors. When using the ultra-low-volume method, it is possible to formulate spray liquors in which the concentration of active substance is preferably from 0.5 to 20 percent by weight, while the spray liquors formulated for the low-volume method and the high-volume method preferably have a concentration of active substance of 0.02 to 1.0 percent by weight, or 0.002 to 0.1 percent by weight, respectively.

The fungicidal compositions according to the invention can be prepared by a process in which at least one compound according to the invention is mixed with formulation adjuvants.

The compositions can be prepared in a known manner, for example by mixing the active substance with solid carriers, by dissolving or suspending the active substance in suitable solvents or dispersion media, if appropriate with the use of tensides as wetting agents or emulsifiers, or of dispersing agents, or by diluting already prepared emulsifiable concentrates with solvents or dispersion media, etc.

In the case of compositions in the form of powders, the active substance can be mixed with a solid carrier, for example by grinding the active substance together with the carrier; or the solid carrier can be impregnated with a solution or suspension of the active substance, and the solvent or dispersion media can then be removed by evaporating, heating or by filtering off with suction, under reduced pressure. By adding tensides or dispersing agents, such compositions in the form of powders can be rendered readily wettable with water, so that they can be converted into aqueous suspensions which are suitable, for example, as sprays.

The compounds according to the invention can also be mixed with a tenside and a solid carrier to form a wettable powder which is dispersible in water, or they can be mixed with a solid, pre-granulated carrier to form a product in the form of granules.

If desired, a compound according to the invention can be dissolved in a water-immiscible solvent, such as, for example, an alicyclic ketone, and this solvent suitably contains a dissolved emulsifier, so that the solution is self-emulsifying on addition to water. Alternatively, the active substance can be mixed with an emulsifier, and the mixture can then be diluted with water to the desired concentration. In addition, the active substance can be dissolved in a solvent, and the solution can then be mixed with an emulsifier. Such a mixture can likewise be-diluted with water to the desired concentration. In this manner, emulsifiable concentrates or ready-to-use emulsions are obtained.

The compositions according to the invention can be applied by the application methods customary in plant protection or agriculture. The process according to the invention for controlling fungi is characterized in that the material to be protected, for example plants, parts of plants or seeds, is treated with an effective amount of a compound according to the invention or a composition according to the invention.

The examples which follow illustrate the invention.

I. MANUFACTURE OF THE ACTIVE SUBSTANCES OF THE FORMULA I

EXAMPLE 1

2.0 g (7.0 mmol) of methyl 2-(α-bromo-o-tolyl)-3-methoxyacrylate and 0.95 g (7.0 mmol) of acetophenone oxime are added at 0° C. to 0.19 g (7.7 mmol) of sodium hydride in 20 ml of dimethylformamide. After the reaction mixture has been stirred for 10 minutes, saturated sodium bicarbonate solution is added, and the mixture is extracted three times using ethyl acetate. The organic phases are dried over anhydrous sodium sulphate. After the solvent has been distilled off, the oil which remains is purified by chromatography on silica gel using diethyl ether/n-hexane (1:1) as the eluent. In this manner, methyl [E] -3-methoxy-2-[α-{[(α-methylbenzyl)imino]oxy}-o-tolyl]-acrylate is obtained as a yellow oil.

EXAMPLE 2

3.67 g (13.2 mmol) of methyl 2-(α-bromo-o-tolyl)-3-methoxy-acrylate and 3.0 g (13.2 mmol) of 4-phenoxyacetophenone oxime in 13 ml of methylene chloride are stirred vigorously for 10 minutes at room temperature with 13 ml of 2.2N sodium hydroxide solution and 5.7 g of tetrabutyl ammonium bisulphate. Identical amounts of methylene chloride, 2.2N sodium hydroxide solution and tetrabutylammonium bisulphate are then added, and stirring is continued for 10 minutes. Again, identical amounts of 2.2N sodium hydroxide solution and tetrabutylammonium bisulphate are subsequently added, and, after the mixture has been stirred for a further 10 minutes, saturated sodium bicarbonate solution.

The mixture is extracted three times with ethyl acetate, and the combined organic phases are washed with saturated sodium chloride solution and dried over anhydrous sodium sulphate. After the solvent has been distilled off, the oil which remains is purified by chromatography on silica gel using n-hexane/diethyl ether (4:1) as the eluent.

In this manner, methyl [E]-3-methoxy-2-[α-{[(α-methyl-4-phenoxybenzyl)imino]oxy}-o-tolyl]-acrylate is obtained as a yellow oil.

EXAMPLES 3–244

Starting from methyl 2-(α-bromo-o-tolyl)-3-methoxyacrylate and the appropriate oxime of the formula II, the compounds of the formula I listed in the table below are obtained in analogy to the process described in Example 1 ("Method 1") or Example 2 ("Method 2"):

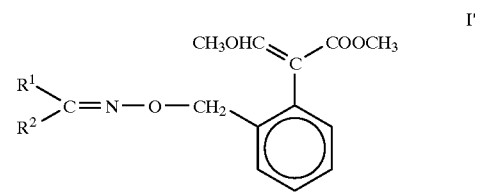

TABLE

| Example | R¹ | R² | Physical data | Method 1/2 |
|---------|-----|-----|---------------|------------|
| 3 | carbamoyl | cyano | mp. 136–137° C. | 1 |
| 4 | 2-furyl | methyl | mp. 77° C. | 1 |
| 5 | benzoyl | ethoxy-carbonyl | oil | 1 |
| 6 | 3,5-di(tri-fluoromethyl)-phenyl | methyl | mp. 112–113° C. | 1 |
| 7 | 2-fluoro-5-methyl-phenyl | methyl | oil | 1 |
| 8 | 2-benzofuranyl | methyl | oil | 1 |
| 9 | 4-chlorophenyl | hydrogen | mp. 119–121° C. | 1 |
| 10 | 2,4-dichloro-phenyl | hydrogen | mp. 111–112° C. | 1 |
| 11 | 3-nitrophenyl | hydrogen | oil | 1 |
| 12 | 2-quinolinyl | hydrogen | mp. 114–115° C. | 1 |
| 13 | 5-methyl-3-methyl thio-4-isoxazolyl | methyl | oil | 1 |
| 14 | phenyl | trifluoro-methyl | oil | 1 |
| 15 | 4-fluorophenyl | methyl | oil | 1 |
| 16 | 4-nitrophenyl | methyl | mp. 145–146° C. | 1 |
| 17 | phenyl | hydrogen | oil | 1 |
| 18 | 2-pyridyl | hydrogen | oil | 1 |
| 19 | 3-pyridyl | hydrogen | oil | 1 |
| 20 | 2-chlorophenyl | hydrogen | mp. 97–98° C. | 1 |
| 21 | benzoyl | hydrogen | oil | 1 |
| 22 | β-phenyl- | hydrogen | mp. 151–152° C. | 1 |

TABLE-continued

| Example | R¹ | R² | Physical data | Method 1/2 |
|---|---|---|---|---|
| 23 | 2-thienyl ethenyl | methyl | mp. 60–61° C. | 1 |
| 24 | 4-chlorophenyl | methyl | mp. 118–119° C. | 1 |
| 25 | phenyl | ethyl | oil | 1 |
| 26 | 4-chlorophenyl | ethyl | oil | 1 |
| 27 | phenyl | n-propyl | oil | 1 |
| 28 | phenyl | cyclopropyl | oil | 1 |
| 29 | ethoxycarbonyl | cyano | mp. 91–92° C. | 1 |
| 30 | benzoyl | methyl | oil | 1 |
| 31 | β-phenyl-ethenyl | methyl | mp. 113–114° C. | 1 |
| 32 | α,α,α-tri fluoro-p-tolyl | hydrogen | mp. 127–128° C. | 1 |
| 33 | 2-pyridyl | methyl | mp. 65–67° C. | 1 |
| 34 | 3-pyridyl | methyl | oil | 1 |
| 35 | 4-pyridyl | methyl | mp. 101–103° C. | 1 |
| 36 | 5-methyl-2-furyl | methyl | oil | 1 |
| 37 | 5-chloro-2-thienyl | methyl | isomer 1: mp. 91–92° C. isomer 2: oil | 1 |
| 38 | 2,4-dimethyl-5-thiazolyl | methyl | oil | 1 |
| 39 | o-tolyl | methyl | oil | 1 |
| 40 | p-anisyl | methyl | mp. 89–90° C. | 1 |
| 41 | 4-biphenylyl | methyl | mp. 117–118° C. | 1 |
| 42 | cyclopropyl | cyclopropyl | oil | 1 |
| 43 | β-(2-furyl)-ethenyl | methyl | oil | 1 |
| 44 | β-(3,4,5-trimethoxy-phenyl)-ethenyl | methyl | oil | 1 |
| 45 | 4-(4-chloro-3-nitrophenyl)-3-methyl-1,3-buta-dienyl | methyl | oil | 1 |
| 46 | 3,4-dichloro-phenyl | hydrogen | mp. 95–96° C. | 1 |
| 47 | 2-naphthyl | hydrogen | oil | 1 |
| 48 | 2-thiazolyl | hydrogen | oil | 1 |
| 49 | α,α,α-tri fluoro-m-tolyl | methyl | mp. 55–56° C. | 1 |
| 50 | 3-bromophenyl | methyl | mp. 73–74° C. | 1 |
| 51 | 2-chlorophenyl | methyl | oil | 1 |
| 52 | 3-nitrophenyl | methyl | oil | 1 |
| 53 | 6-chloro-2-dibenzofuryl | methoxy-carbonyl | mp. 129–130° C. | 1 |
| 54 | phenyl | phenyl | oil | 1 |
| 55 | 5-chloro-3-methyl-2-benzo-thienyl | methyl | mp. 112–113° C. | 1 |
| 56 | 3-chlorophenyl | methyl | oil | 1 |
| 57 | 3,4-dichloro-phenyl | | mp. 82–83° C. | 1 |
| 58 | 2,4-dichloro-phenyl | methyl | isomer 1: oil isomer 2: oil | 1 |
| 59 | 2-naphthyl | methyl | oil | 1 |
| 60 | α-methoxy-imino-2,4-dichlorobenzyl | hydrogen | oil | 1 |
| 61 | phenyl | n-butyl | oil | 1 |
| 62 | 2,5-dimethyl-3-thienyl | methyl | mp. 68–69° C. | 2 |
| 63 | phenyl | isopropyl | oil | 1 |
| 64 | phenyl | cyclohexyl | oil | 1 |
| 65 | 2-(p-tert.butyl-phenyl)-1-methyl-ethenyl | hydrogen | oil | 1 |
| 66 | 2,4-dichloro-benzyl | 3-pyridyl | oil | 1 |
| 67 | 2,4-chloro-phenyl | 3-pyridyl-methyl | oil | 1 |
| 68 | 3-methyl-2-benzothienyl | methyl | mp. 85–86° C. | 1 |
| 69 | 3,5-dimethyl-2-furyl | methyl | mp. 96–97° C. | 1 |
| 70 | 1-naphthyl | hydrogen | oil | 1 |
| 71 | β-(4-methoxy-phenyl)-ethenyl | hydrogen | mp. 83–87° C. | 1 |
| 72 | m-tolyl | hydrogen | oil | 1 |
| 73 | 2-fluorophenyl | hydrogen | mp. 83–84° C. | 1 |
| 74 | 3-fluorophenyl | hydrogen | mp. 82–83° C. | 1 |
| 75 | 4-fluorophenyl | hydrogen | isomer 1: mp. 92–93° C. isomer 2: oil | 1 |
| 76 | 6-methoxy-2-naphthyl | hydrogen | oil | 1 |
| 77 | 3-chlorophenyl | hydrogen | oil | 1 |
| 78 | 3-bromophenyl | hydrogen | oil | 1 |
| 79 | 4-bromophenyl | hydrogen | mp. 142–143° C. | 1 |
| 80 | 3-methyl-2-naphtyl | hydrogen | oil | 1 |
| 81 | 2,3-difluoro-phenyl | hydrogen | oil | 1 |
| 82 | p-tolyl | hydrogen | mp. 93–94° C. | 1 |
| 83 | 2-thienyl | hydrogen | oil | 1 |
| 84 | 2,5-difluoro-phenyl | hydrogen | oil | 1 |
| 85 | 2-fluoro-6-chlorophenyl | hydrogen | mp. 70–73° C. | 1 |
| 86 | 3-phenoxy-phenyl | hydrogen | oil | 1 |
| 87 | 4-ethylphenyl | hydrogen | oil | 1 |
| 88 | 3-thienyl | hydrogen | isomer 1: mp. 125–126° C. isomer 2: oil | 1 |
| 89 | β-(2-quinolin-yl)-ethenyl | hydrogen | oil | 1 |
| 90 | β-(3-thienyl)-ethenyl | hydrogen | oil | 1 |
| 91 | α,α,α-tri-fluoro-m-tolyl | hydrogen | oil | 1 |
| 92 | β-(N-methyl-2-pyrrolyl)-ethenyl | hydrogen | oil | 1 |
| 93 | 4-bromophenyl | methyl | mp. 123–124° C. | 1 |
| 94 | 2,5-dichloro-phenyl | methyl | isomer 1: mp. 92–93° C. isomer 2: oil | 1 |
| 95 | 4-ethylphenyl | methyl | oil | 2 |
| 96 | 3-ethylphenyl | methyl | oil | 2 |
| 97 | 3,4-dimethyl-phenyl | methyl | mp. 88–89° C. | 2 |
| 98 | 2,4-dimethyl-phenyl | methyl | oil | 2 |
| 99 | 2-fluorophenyl | methyl | 73–74° C. | 1 |
| 100 | m-tolyl | methyl | mp. 75° C. | 2 |
| 101 | p-tolyl | methyl | 77–78° C. | 2 |
| 102 | 6-methyl-2-naphthyl | methyl | oil | 2 |
| 103 | 5-bromo-2-thienyl | methyl | isomer 1: mp. 98° C. isomer 2: oil | 1 |
| 104 | 2-thienyl | tert.butyl | oil | 1 |
| 105 | 1-naphthyl | methyl | mp. 118.5–121° C. | 1 |
| 106 | 2-naphthyl | cyclopropyl | oil | 1 |
| 107 | 2-naphthyl | ethyl | oil | 1 |
| 108 | 4-difluoro-methoxyphenyl | methyl | mp. 102–103° C. | 1 |
| 109 | 4-chlorophenyl | neopentyl | oil | 1 |
| 110 | 2-naphthyl | n-propyl | oil | 1 |
| 111 | 3,5-di(trifluoro-methyl)-phenyl | ethyl | isomer 1: oil isomer 2: oil | 1 |
| 112 | 5,6,7,8-tetra-hydro-2-naphthyl | methyl | mp. 97–98° C. | 2 |
| 113 | α,α,α-tri-fluoro- | methyl | mp. 123–124° C. | 1 |

TABLE-continued

| Example | R¹ | R² | Physical data | Method 1/2 |
|---|---|---|---|---|
| | p-tolyl | | | |
| 114 | 3-phenanthryl | methyl | oil | 2 |
| 115 | 2-fluorenyl | methyl | oil | 2 |
| 116 | isopropyl | methyl | oil | 2 |
| 117 | 4-chlorophenyl | n-propyl | oil | 1 |
| 118 | 4-chlorophenyl | cyclopropyl | oil | 1 |
| 119 | 3-methoxyphenyl | methyl | mp. 86–87° C. | 1 |
| 120 | 3-chlorophenyl | ethyl | oil | 1 |
| 121 | 4-fluorophenyl | ethyl | isomer 1: oil isomer 2: oil | 1 |
| 122 | 4-bromophenyl | ethyl | mp. 108° C. | 1 |
| 123 | 4-tert.butylphenyl | methyl | mp. 105–106° C. | 2 |
| 124 | 3-thienyl | methyl | mp. 87–88° C. | 1 |
| 125 | cyclopropyl | methyl | oil | 2 |
| 126 | 2-quinolinylmethyl | methyl | oil | 2 |
| 127 | 3-fluoro-5-trifluoromethylphenyl | methyl | mp. 102–103° C. | 1 |
| 128 | 3-fluorophenyl | methyl | oil | 1 |
| 129 | 3,5-difluorophenyl | methyl | oil | 1 |
| 130 | 3,5-difluorophenyl | ethyl | oil | 1 |
| 131 | 2-fluorophenyl | ethyl | isomer 1: oil isomer 2: oil | 1 |
| 132 | 3,4-dimethoxyphenyl | methyl | oil | 2 |
| 133 | p-tolyl | ethyl | oil | 2 |
| 134 | 2,5-dimethyl-3-furyl | methyl | oil | 2 |
| 135 | phenyl | methylthiomethyl | isomer 1: oil isomer 2: oil | 1 |
| 136 | 2-thiazolinyl | methylio | mp. 81–83° C. | 1 |
| 137 | benzyl | methyl | oil | 2 |
| 138 | 3-trifluoromethoxyphenyl | methyl | oil | 1 |
| 139 | 3-fluoro-5-trifluoromethylphenyl | ethyl | isomer 1: oil isomer 2: oil | 1 |
| 140 | 3,4,5-trimethoxyphenyl | methyl | oil | 2 |
| 141 | 2-nitrophenyl | methyl | oil | 1 |
| 142 | cyclohexyl | methyl | oil | 2 |
| 143 | phenylthiomethyl | methyl | isomer 1: oil isomer 2: oil | 2 |
| 144 | 4-chlorophenyl | trifluoromethyl | oil | 1 |
| 145 | 2-thienyl | cyclopropyl | oil | 1 |
| 146 | 3,4-dimethoxybenzyl | methyl | oil | 1 |
| 147 | α,α,α-trifluoro-m-tolyl | trifluoromethyl | oil | 1 |
| 148 | α,α,α-trifluoro-m-tolyl | ethyl | oil | 1 |
| 149 | 3,5-dichlorophenyl | methyl | oil | 1 |
| 150 | β-(2-naphtyl)-ethenyl | trifluoromethyl | oil | 1 |
| 151 | 2-naphtyl | methyl | oil | 1 |
| 152 | phenyl | methoxymethyl | isomer 1: oil ospmer 2: oil | 1 |
| 153 | phenoxymethyl | methyl | oil | 1 |
| 154 | methyl | methyl | oil | 2 |
| 155 | α,α,α-trifluoro-m-tolyl | n-propyl | oil | 1 |
| 156 | α,α,α-trifluoro-m-tolyl | methoxymethyl | isomer 1: oil isomer 2: oil | 1 |
| 157 | 2-pyridyl | n-propyl | oil | 1 |
| 158 | α,α,α-trifluoro-m-tolyl | cyclopropyl | oil | 1 |
| 159 | 2-pyridyl | cyclopropyl | oil | 1 |
| 160 | 2-pyridyl | methoxymethyl | oil | 1 |
| 161 | 2-chloro-5-trifluoromethylphenyl | methyl | isomer 1: oil isomer 2: oil | 1 |
| 162 | 2-methlthio-5-trifluoromethyl- | methyl | isomer 1: oil isomer 2: oil | 1 |
| 163 | 4-chloro-3-trifluoromethylbenzyl | methyl | oil | 1 |
| 164 | 4-methoxybenzyl | methyl | oil | 1 |
| 165 | 3-pyridyl | ethyl | oil | 1 |
| 166 | α,α,α-trifluoro-m-tolyl | isopropyl | oil | 1 |
| 167 | α,α,α-trifluoro-o-tolyl | methyl | oil | 1 |
| 168 | α,α,α-trifluoro-m-tolyl | ααα-trifluoro-m-tolyl | oil | 1 |
| 169 | 4-ethoxyphenyl | methyl | m. p. 79–80° C. | 2 |
| 170 | N-methyl-2-pyrrolyl | methyl | oil | 1 |
| 171 | 10,11-dihydro-5H-dibenzo-[b.f]azepin-2-yl | methyl | oil | 1 |
| 172 | 3-chloro-4-fluoro-phenyl | methyl | m.p. 85° C. | 1 |
| 173 | 2,3-dichlorophenyl | methyl | isomer 1: oil isomer 2: oil | 1 |
| 174 | p-tolyl | trifluoromethyl | oil | 1 |
| 175 | 4-phenylthiophenyl | methyl | oil | 2 |
| 176 | 4-(2,4-dichlorophenoxy)-phenyl | methyl | oil | 2 |
| 177 | 4-(4-nitrophenoxy)phenyl | methyl | oil | 2 |
| 178 | 4-(4-methoxyphenoxy)-phenyl | methyl | oil | 2 |
| 179 | 3,4-methylene dioxyphenyl | methyl | oil | 2 |
| 180 | 7-benzodioxynal | methyl | oil | 2 |
| 181 | 2,5-dichloro-3-thienyl | methyl | isomer 1: oil isomer 2: oil | 1 |
| 182 | 2-thienyl | ethyl | isomer 1: oil isomer 2: oil | 1 |
| 183 | 2-chlorophenoxymethyl | methyl | oil | 1 |
| 184 | o-tolyl | methoxycarbonyl | isomer 1: m. p. 101–103° C. isomer 2: m. p. 85–86° C. | 1 |
| 185 | 3-bromophenyl | ethyl | oil | 1 |
| 186 | 3-fluoro-5-trifluoromethylphenyl | cyclopropyl | oil | 1 |
| 187 | 2,3,4-trichlorophenyl | methyl | m. p. 96–97° C. | 1 |
| 188 | 4-chloro-3-methylphenyl | methyl | m. p. 88° C. | 1 |
| 189 | p-tolyl | n-propyl | oil | 1 |
| 190 | 5-methyl-2- | methyl | isomer 1: oil | 1 |

TABLE-continued

| Example | R¹ | R² | Physical data | Method 1/2 |
|---|---|---|---|---|
| | thienyl | | isomer 2: oil | |
| 191 | 2-thienyl | n-propyl | isomer 1: oil<br>isomer 2: oil | 1 |
| 192 | 4-phenoxy-phenyl | cyclo-propyl | oil | 2 |
| 193 | 3-bromophenyl | cyclo-propyl | oil | 1 |
| 194 | 3-chlorophenyl | cyclo-propyl | oil | 1 |
| 195 | 3-fluorophenyl | cyclo-propyl | oil | 1 |
| 196 | 2-thiazolyl | cyclo-propyl | isomer 1: oil<br>isomer 2:<br>m. p. 71–72° C. | 1 |
| 197 | 3-bromophenyl | n-propyl | oil | 1 |
| 198 | 3-chlorophenyl | n-propyl | oil | 1 |
| 199 | 4-fluoro-3-tri-fluoromethyl-phenyl | n-propyl | oil | 1 |
| 200 | 3-fluorophenyl | n-propyl | oil | 1 |
| 201 | 4-phenoxy-phenyl | n-propyl | oil | 2 |
| 202 | 3-fluoro-5-tri-fluoromethyl-phenyl | n-propyl | oil | 1 |
| 203 | 2-thiazolyl | n-propyl | oil | 1 |
| 204 | 3-bromophenyl | trifluoro-methyl | oil | 1 |
| 205 | 3-chlorophenyl | methyl | oil | 1 |
| 206 | 2-thiazolyl | methyl | m. p. 97–98° C. | 1 |
| 207 | 4-phenoxy-phenyl | methyl | oil | 1 |
| 208 | 2-pridyl | methyl | oil | 1 |
| 209 | 3-bromophenyl | isopropyl | oil | 2 |
| 210 | 3-chlorophenyl | isopropyl | oil | 2 |
| 211 | 2-pyridyl | isopropyl | isomer 1: oil<br>isomer 2: oil | 1 |
| 212 | 4-phenoxy-phenyl | isopropyl | oil | 2 |
| 213 | 3-bromophenyl | methoxy-methyl | isomer 1: oil<br>isomer 2: oil | 1 |
| 214 | 4-fluoro-3-tri-fluoromethyl-phenyl | methyl | isomer 1: oil<br>isomer 2: oil | 1 |
| 215 | 4-fluoro-3-tri-fluoromethyl-phenyl | cyclco-propyl | oil | 1 |
| 216 | 2-bromophenyl | methyl | oil | 1 |
| 217 | 4-fluorophenyl | cyclo-propyl | oil | 1 |
| 218 | 4-(n-propyl)-phenyl | methyl | oil | 2 |
| 219 | 4-methoxy-3-nitro-phenyl | methyl | m. p. 131–132° C. | 1 |
| 220 | 2,3-dihydro-5-benzo[b]furyl | methyl | oil | 2 |
| 221 | 2-methoxy-phenyl | methyl | oil | 1 |
| 222 | 2,4-dimethoxy-phenyl | methyl | oil | 2 |
| 223 | 4-fluoro-3-tri-fluoromethyl-phenyl | isopropyl | oil | 1 |
| 224 | 3-chlorophenyl | methoxy-methyl | isomer 1: oil<br>isomer 2: oil | 1 |
| 225 | 3-iodophenyl | methyl | m. p. 103° C. | 1 |
| 226 | 4-iodophenyl | methyl | m. p. 124° C. | 1 |
| 227 | 2-naphthyl | methoxy-methyl | oil | 1 |
| 228 | 2-(4-methoxy-phenyl)-ether | methyl | oil | 1 |
| 229 | 1,4,8-trimethyl-nona-1,3,7-trienyl | methyl | oil | 1 |
| 230 | 1-methyl-2-(3,4-methyl- | methyl | oil | 1 |

TABLE-continued

| Example | R¹ | R² | Physical data | Method 1/2 |
|---|---|---|---|---|
| | enedioxy-phenyl)-ethyl | | | |
| 231 | (4-fluoro-phenyl)-carbamoyl | hydrogen | oil | 2 |

$$\begin{matrix} & R^1 \\ & | \\ & C \\ & | \\ & R^2 \end{matrix}$$

| Example | | Physical data | Method 1/2 |
|---|---|---|---|
| 232 | (bicyclic structure: two fused benzene rings connected via cyclohexane to C) | oil | 1 |
| 233 | (tetrahydronaphthyl-C) | oil | 1 |
| 234 | (chromanyl-C with O) | oil | 1 |
| 235 | (thiochromanyl-C with S) | oil | 1 |
| 236 | (chloro-thiochromanyl-C with Cl and S) | oil | 1 |

-continued

| Example | $\overset{R^1}{\underset{R^2}{\diagdown}}C$ | Physical data | Method 1/2 |
|---|---|---|---|
| 237 | [2-chloro dibenzofuran-like structure with O] | oil | 1 |
| 238 | [6-chloro-sulfone thiochroman structure] | oil | 1 |
| 239 | [methyl, fluoro-substituted thioxanthene-like structure] | oil | 1 |
| 240 | [SCH₃-substituted thioxanthene structure] | oil | 1 |
| 241 | [CH₃-substituted thioxanthene structure] | oil | 1 |

-continued

| Example | $\overset{R^1}{\underset{R^2}{\diagdown}}C$ | Physical data | Method 1/2 |
|---|---|---|---|
| 242 | [chloro thiochromene structure] | oil | 1 |
| 243 | [chloro, methyl thiochroman structure] | oil | 1 |
| 244 | [chloro, methyl sulfone thiochroman structure] | oil | 1 |

II. FORMULATION EXAMPLES

EXAMPLE 245

An emulsifiable concentrate has the following composition:

|  | g/liter |
|---|---|
| Active substance (compound according to the invention) | 100 |
| Nonylphenol (10) ethoxylate (nonionic emulsifier) | 50 |
| Calcium dodecylbenzenesulphonate (anionic emulsifier) | 25 |
| N-methyl-2-pyrrolidone (solubilizer) | 200 |
| Mixture of alkylbenzenes (solvent) | to 1 l |

The active substance and the emulsifiers are dissolved in the solvent and the solubilizer. A ready-to-use spray liquor of any desired concentration can be prepared by emulsifying this concentrate in water.

EXAMPLE 246

A wettable powder has the following composition:

|  | Percent by weight |
|---|---|
| Active substance (compound according to the invention) | 25.0 |
| Silica (hydratised; carrier) | 20.0 |
| Sodium lauryl sulphate (wetting agent) | 2.0 |
| Sodium lignosulphonate (dispersing agent) | 4.0 |
| Kaolin (carrier) | 49.0 |

The components are mixed with each other, and the mixture is ground finely in a suitable mill. Dispersing the mixture in water results in a suspension which is suitable as a ready-to-use spray liquor.

EXAMPLES 247–307

Examples 247–307 are prepared in a similar fashion to Example 1:

| Example | $R^1$ | $R^2$ | Physical Data (m. p. and/or $^1$H NMR {**}) |
|---|---|---|---|
| 247 | α-(methoxyimino)-3-chlorobenzyl | methyl | 175–177° C. |
| 248 | α-(methoxyimino)-4-methoxybenzyl | methyl | 104–106° C. |
| 249 | α-(methoxyimino)-3-fluoro-5-trifluoromethylbenzyl | methyl | 164–166° C. |
| 250 | α-(methoxyimino)-benzyl | methyl | 141–143° C. |
| 251 | α-(methoxyimino)-3-bromobenzyl | methyl | 176–178° C. |
| 252 | α-(methoxyimino)-4-allyloxybenzyl | methyl | isomer 1: 77–80° C.; isomer 2: 2.08** |
| 253 | α-(methoxyimino)-4-methylbenzyl | ethyl | isomer 1: 3.90**; isomer 2: 3.97** |
| 254 | α-(methoxyimino)-4-isobutylbenzyl | methyl | isomer 1: 2.11**; isomer 2: 2.08** |
| 255 | α-(methoxyimino)-4-propargyloxybenzyl | methyl | 2.06/2.11** (E/Z) |
| 256 | α-(methoxyimino)-4-(2,2,2-trifluoroethoxybenzyl | methyl | isomer 1: 2.11**; isomer 2: 2.07** |
| 257 | α-(methoxyimino)-4-ethoxybenzyl | methyl | isomer 1: 93–95° C. isomer 2: 2.06** |
| 258 | α-(methoxyimino)-4-methylbenzyl | cyano | 98–133° C. (E/Z) |
| 259 | α-(methoxyimino)-4-chlorobenzyl | cyano | 106–108° C. |
| 260 | α-(methoxyimino)-3,4-dichlorobenzyl | cyano | 128–130° C.; 109–111° C. (E/Z) |
| 261 | α-(methoxyimino)-4-trifluoromethoxybenzyl | cyano | oil (E/Z) |
| 262 | α-(methoxyimino)-3-trifluoromethylbenzyl | cyano |  |
| 263 | α-(methoxyimino)-2-chlorobenzyl | cyano |  |
| 264 | α-(methoxyimino)-4-fluorobenzyl | cyano |  |
| 265 | α-(methoxyimino)-4-phenoxybenzyl | methyl | isomer 1: 112–114° C.; isomer 2: oil |
| 266 | α-(methoxyimino)-4-(3,3-dichloro-prop-2-enyloxybenzyl | methyl |  |
| 267 | α-(methoxyimino)-4-(3,3-difluoro-prop-2-enyloxybenzyl | methyl |  |
| 268 | α-(methoxyimino)-4-(3,3-dibromo-prop-2-enyloxybenzyl | methyl |  |
| 269 | α-(methoxyimino)-4-{-4-chloro-phenox}benzyl | methyl | isomer 1: oil; isomer 2: resin |
| 270 | α-(methoxyimino)-4-{-4-fluoro-phenox}benzyl | methyl | isomer 1: 126–128° C.; isomer 2: oil |
| 271 | α-(methoxyimino)-4-phenoxymethylbenzyl | methyl | isomer 1: resin; isomer 2: resin |
| 272 | α-(methoxyimino)-4-benzyloxybenzyl | methyl | oil |
| 273 | α-(methoxyimino)-n-propoxybenzyl | methyl | isomer 1: oil; isomer 2: oil |
| 274 | α-(methoxyimino)-4-(3,3-dimethyl-allyloxy)benzyl | methyl | isomer 1: 107–110° C.; isomer 2: oil |
| 275 | α-(methoxyimino)-4-{2-methylprop-2-enyloxy}benzyl | methyl | isomer 1: 97–99° C.; isomer 2: oil |
| 276 | α-(methoxyimino)-4-{3-methylprop-2-enyloxy}benzyl | methyl | isomer 1: oil; isomer 2: oil |
| 277 | α-(methoxyimino)-4-prop-2-enyl-oxybenzyl | methyl | isomer 1: 74–76° C. |
| 278 | α-(methoxyimino)-4-propargyloxybenzyl | methyl | oil |
| 279 | α-(methoxyimino)-4-(3-trifluoromethylbenzyloxy)benzyl | methyl | isomer 1: 83–85° C.; isomer 2: resin |
| 280 | α-(methoxyimino)-4-(3-trifluoromethylphenoxy)benzyl | methyl | isomer 1: 127–128° C.; isomer 2: oil |
| 281 | α-(methoxyimino)-4-benzyloxybenzyl | methyl | isomer 1: oil; isomer 2: oil |
| 282 | α-(methoxyimino)-4-(4-fluorobenzyloxy)benzyl | methyl | isomer 1: oil; isomer 2: oil |
| 283 | α-(methoxyimino)-4-methylthiobenzyl | methyl | isomer 1: 119–121° C. isomer 2: resin |
| 284 | α-(methoxyimino)-4-(4-trifluoromethylbenzyloxy)benzyl | methyl | isomer 1: 82–84° C.; isomer 2: 89–91° C. |
| 285 | α-(methoxyimino)-4-(4-bromo-benzyloxy)benzyl | methyl |  |
| 286 | α-(methoxyimino)-4-(4-methyl-benzyloxy)benzyl | methyl |  |
| 287 | α-(methoxyimino)-4-(4-methoxy-benzyloxy)benzyl | methyl |  |
| 288 | α-(methoxyimino)-4-(2-trifluoromethylbenzyloxy)benzyl | methyl | isomer 1: 25–129° C.; isomer 2: resin |
| 289 | α-(methoxyimino)-4-(2-fluoro-benzyloxy)benzyl | methyl | isomer 1: oil; isomer 2: oil |
| 290 | α-(methoxyimino)-4-(2-chloro-benzyloxy)benzyl | methyl |  |
| 291 | α-(methoxyimino)-4-(2-bromo-benzyloxy)benzyl | methyl |  |
| 292 | α-(methoxyimino)-4-(3-fluoro-benzyloxy)benzyl | methyl | isomer 1: 111; 112° C; isomer 2: oil |
| 293 | α-(methoxyimino)-4-(3-chloro-benzyloxy)benzyl | methyl | isomer 1: oil; isomer 2: oil |
| 294 | α-(methoxyimino)-4-(3-bromo-benzyloxy)benzyl | methyl | isomer 1: resin; isomer 2: resin |
| 295 | α-(methoxyimino)benzyl | cyano | oil |
| 296 | α-(methoxyimino)-4-methoxybenzyl | cyano | isomer 1: 136–138° C.; isomer 2: resin |
| 297 | α-(methoxyimino)-4-t-butylbenzyl | cyano | oil |
| 298 | α-(methoxyimino)-4-phenoxybenzyl | cyano | oil |
| 299 | α-(methoxyimino)-4-(1,1-difluoro-2,2-dichloroethoxy)benzyl | methyl |  |
| 300 | α-(methoxyimino)-4-(1,1-difluoro-2,2-dibromoethoxy)benzyl | methyl |  |
| 301 | α-(methoxyimino)-4-t-butylbenzyl | methyl | isomer 1: resin; |

-continued

| Example | R$^1$ | R$^2$ | Physical Data (m. p. and/or $^1$H NMR {**}) |
|---|---|---|---|
| | | | isomer 2: oil |
| 302 | α-(methoxyimino)-4-(4-chloro-benzyloxy)benzyl | | |
| 303 | α-(methoxyimino)-4-(2-chloro-1,1,2-trifluoroethoxy)benzyl | methyl | isomer 1: 75–76° C. |
| 304 | α-(methoxyimino)-4-(2-bromo-1,1,2-trifluoroethoxy)benzyl | methyl | isomer 1: resin |
| 305 | α-(methoxyimino)-4-(1,1,2,3,3,3-hexfluoropropoxy)benzyl | methyl | isomer 1: 82–84° C. |
| 306 | α-(methoxyimino)-4-ethyl-thiobenzyl | methyl | isomer 1: oil; isomer 2: oil |
| 307 | α-(methoxyimino)-4-n-propylthio-benzyl | methyl | isomer 1: oil isomer 2: oil |

What is claimed is:

1. A compound of the formula:

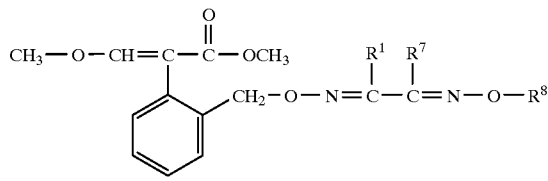

wherein

R$_1$ is hydrogen, C$_{1-2}$alkyl, C$_{1-4}$haloalkyl, C$_{1-4}$alkoxyC$_{1-4}$alkyl, C$_{1-4}$alkylthioC$_{1-4}$alkyl, unsubstituted or substituted arylC$_{1-4}$alkyl, unsubstituted or substituted aryloxyC$_{1-4}$alkyl, unsubstituted or substituted arylthioC$_{1-4}$alkyl, C$_{2-12}$alkenyl, unsubstituted or substituted arylC$_{2-4}$alkenyl, C$_{2-12}$alkynyl, C$_{3-6}$cycloalkyl, unsubstituted or substituted aryl, cyano, —COOR$^3$, —CONR$^4$R$^5$, —COR$^6$, or —CR$^7$=NOR$^8$; and R$^7$ is aryl, unsubstituted or substituted with one or more members selected from the group consisting of halogen, C$_{1-4}$alkyl, C$_{1-4}$haloalkyl, C$_{1-4}$alkoxyC$_{1-4}$alkyl, arylC$_{1-4}$alkyl, heteroarylC$_{1-4}$alkyl, aryloxyC$_{1-4}$alkyl, heteroaryloxyC$_{1-4}$alkyl, C$_{2-4}$alkenyl, arylC$_{2-4}$alkenyl, heteroarylC$_{2-4}$alkenyl, C$_{2-4}$alkynyl, C$_{3-6}$cycloalkyl, aryl, heteroaryl, C$_{1-4}$alkoxy, C$_{1-4}$haloalkoxy, arylC$_{1-4}$alkoxy, heteroarylC$_{1-4}$alkoxy, C$_{2-4}$alkenyloxy, C$_{2-4}$alkynyloxy, aryloxy, heteroaryloxy, C$_{1-4}$alkylthio, cyano, nitro, NR$^9$R$^{10}$, COR$^{11}$, or COOR$^{12}$;

each of R$^3$, R$^4$, R$^5$, R$^6$, and R$^8$, independently of the other, is hydrogen, C$_{1-4}$-alkyl, or unsubstituted or substituted aryl, in which when aryl is substituted, the substituents are one or more members selected from the group consisting of halogen, C$_{1-4}$alkyl, C$_{1-4}$haloalkyl, C$_{1-4}$alkoxyC$_{1-4}$alkyl, arylC$_{1-4}$alkyl, heteroarylC$_{1-4}$alkyl, aryloxyC$_{1-4}$alkyl, heteroaryloxyC$_{1-4}$alkyl, C$_{2-4}$alkenyl, arylC$_{2-4}$alkenyl, heteroarylC$_{2-4}$alkenyl, C$_{2-4}$alkynyl, C$_{3-6}$cycloalkyl, aryl, heteroaryl, C$_{1-4}$alkoxy, C$_{1-4}$haloalkoxy, arylC$_{1-4}$alkoxy, heteroarylC$_{1-4}$alkoxy, C$_{2-4}$alkenyloxy, C$_{2-4}$alkynyloxy, aryloxy, heteroaryloxy, C$_{1-4}$alkylthio, cyano, nitro, NR$^9$R$^{10}$, COR$^{11}$, or COOR$^{12}$; and each of R$^9$, R$^{10}$, R$^{11}$, and R$^{12}$ is C$_{1-4}$alkyl or aryl.

2. A compound according to claim 1 in which R$^1$ is hydrogen, C$_{1-12}$alkyl, C$_{1-4}$haloalkyl, arylC$_{1-4}$alkyl, C$_{2-12}$alkenyl, arylC$_{2-4}$alkenyl, C$_{2-12}$alkynyl, C$_{3-6}$cycloalkyl, aryl, cyano, —COOR$^3$, —CONR$^4$R$^5$, —COR$^6$, or —CR$^7$=NOR$^8$.

3. A compound according to claim 1 in which R$^7$ is phenyl, unsubstituted or substituted with from one to three substituents, each of which is halogen, C$_{1-4}$-alkyl, or C$_{1-4}$haloalkyl.

4. A compound according to claim 1 in which R$^7$ is aryl substituted with aryl-C$_{1-4}$alkoxy or aryloxy wherein each of said aryl groups is unsubstituted or substituted with halogen, C$_{1-4}$alkyl, C$_{1-4}$haloalkyl, C$_{1-4}$alkoxy, or C$_{1-4}$haloalkoxy.

5. A compound according to claim 4 in which aryl is phenyl, arylC$_{1-4}$alkoxy is benzoxy, and aryloxy is phenoxy.

6. A compound according to claim 1 in which R$^7$ is arylC$_{1-4}$alkoxy or aryloxy wherein each of said aryl groups is unsubstituted or substituted with halogen, C$_{1-4}$alkyl, C$_{1-4}$haloalkyl, C$_{1-4}$alkoxy, or C$_{1-4}$haloalkoxy.

7. A compound according to claim 6 in which arylC$_{1-4}$alkoxy is benzoxy and aryloxy is phenoxy.

8. A compound according to claim 1 in the E-isomeric form.

9. A fungicidal composition comprising a compound according to claim 1 and a carrier.

10. A compound of the formula:

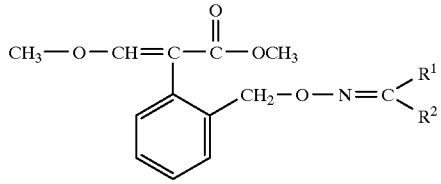

wherein

R$^1$ is hydrogen, C$_{1-12}$alkyl, C$_{1-4}$haloalkyl, C$_{1-4}$alkoxyC$_{1-4}$alkyl, C$_{1-4}$alkylthioC$_{1-4}$alkyl, unsubstituted or substituted arylC$_{1-4}$alkyl, unsubstituted or substituted aryloxyC$_{1-4}$alkyl, unsubstituted or substituted arylthioC$_{1-4}$alkyl, C$_{2-12}$alkenyl, unsubstituted or substituted arylC$_{2-4}$alkenyl, C$_{2-12}$alkynyl, C$_{3-6}$cycloalkyl, unsubstituted or substituted aryl, cyano, —COOR$^3$, —CONR$^4$R$^5$, or —COR$^6$;

R$^2$ is C$_{1-4}$alkylthioC$_{1-4}$alkyl, C$_{1-4}$alkoxyC$_{1-4}$alkyl, C$_{1-4}$haloalkyl, or unsubstituted or substituted arylthioC$_{1-4}$alkyl; and each of R$^3$, R$^4$, R$^5$, and R$^6$, independently of the other, is hydrogen, C$_{1-4}$alkyl, or unsubstituted or substituted aryl, in which when aryl is substituted, the substituents are one or more members selected from the group consisting of halogen, C$_{1-4}$alkyl, C$_{1-4}$haloalkyl, C$_{1-4}$alkoxyC$_{1-4}$alkyl, arylC$_{1-4}$alkyl, heteroarylC$_{1-4}$alkyl, aryloxyC$_{1-4}$alkyl, heteroaryloxyC$_{1-4}$alkyl, C$_{2-4}$alkenyl, arylC$_{2-4}$-alkenyl, heteroarylC$_{2-4}$alkenyl, C$_{2-4}$alkynyl, C$_{3-6}$cycloalkyl, aryl, heteroaryl, C$_{1-4}$alkoxy, C$_{1-4}$haloalkoxy, arylC$_{1-4}$alkoxy, heteroarylC$_{1-4}$alkoxy, C$_{2-4}$alkenyloxy, C$_{2-4}$alkynyloxy, aryloxy, heteroaryloxy, C$_{1-4}$alkylthio, cyano, nitro, NR$^9$R$^{10}$, COR$^{11}$, or COOR$^{12}$, in which each of R$^9$, R$^{10}$, R$^{11}$, and R$^{12}$ is C$_{1-4}$alkyl or aryl.

11. A compound according to claim 10 in which R$^1$ is hydrogen, C$_{1-12}$alkyl, C$_{1-4}$haloalkyl, arylC$_{1-4}$alkyl, C$_{2-12}$alkenyl, arylC$_{2-4}$alkenyl, C$_{2-12}$alkynyl, C$_{3-6}$cycloalkyl, aryl, cyano, —COOR$^3$, —CONR$^4$R$^5$, or —COR$^6$.

12. A compound according to claim 10 in which R$^7$ is phenyl, unsubstituted or substituted with from one to three substituents, each of which is halogen, C$_{1-4}$-alkyl, or C$_{1-4}$haloalkyl.

13. A compound according to claim 10 in the E-isomeric form.

14. A compound according to claim 10 which is methyl 3-methoxy-2-[α-{α-(methylthiomethyl)benzyliminooxy}-o-tolyl]acrylate, methyl 3-methoxy-2-[α(1-phenylthioprop-2-yliminooxy)-o-tolyl]acrylate, methyl 3-methoxy-2-[α-{α-(methoxymethyl)benzyliminooxy}-o-tolyl]acrylate, methyl 3-methoxy-2-[α-{α-(methoxymethyl)-3-trifluoromethylbenzyliminooxy}-o-tolyl]acrylate, methyl 3-methoxy-2-[α-{α-(methoxymethyl)-3-bromobenzyliminooxy}-o-tolyl]acrylate, methyl 3-methoxy-2-[α-{α-(methoxymethyl)-3-chlorobenzyliminooxy}-o-tolyl]acrylate, methyl 3-methoxy-2-[α-(1-{naphth-2-yl}-2-methoxyethyliminooxy)-o-tolyl]acrylate, methyl 3-methoxy-2-[α-{α-trifluoromethyl-4-chlorobenzyliminooxy}-o-tolyl]acrylate, methyl 3-methoxy-2-[α-{α-trifluoromethyl-3-trifluoromethylbenzyliminooxy}-o-tolyl]acrylate, methyl 3-methoxy-2-[α-{1-(naphth-2-yl)-3,3,3-trifluoroprop-1-en-2-yliminooxy}-o-tolyl]acrylate, methyl 3-methoxy-2-[α-{α-(3-trifluoromethylphenyl)-3-trifluoromethylbenzyliminooxy}-o-tolyl]acrylate, methyl 3-methoxy-2-[α-{α-trifluoromethyl-4-methylbenzyliminooxy}-o-tolyl]acrylate, or methyl 3-methoxy-2-[α-{α-trifluoromethyl-3-bromobenzyliminooxy}-o-tolyl]acrylate.

15. A fungicidal composition comprising a compound according to claim 10 and a carrier.

* * * * *